United States Patent [19]
Chan

[11] Patent Number: 5,922,756
[45] Date of Patent: Jul. 13, 1999

[54] METHOD OF INHIBITING NITRIC OXIDE SYNTHASE

[76] Inventor: Marion Man-Ying Chan, 58 Mitchell Ave., Piscataway, N.J. 08854

[21] Appl. No.: 09/024,005

[22] Filed: Feb. 14, 1998

[51] Int. Cl.$^6$ .................................................... A61K 31/35
[52] U.S. Cl. .............................................................. 514/456
[58] Field of Search .............................................. 514/456

[56] References Cited

U.S. PATENT DOCUMENTS

| | | | |
|---|---|---|---|
| 5,318,986 | 6/1994 | Hara et al. | 514/456 |
| 5,391,568 | 2/1995 | Chung | 514/456 |
| 5,449,688 | 9/1995 | Wahl et al. | 514/546 |
| 5,585,402 | 12/1996 | Moncada et al. | 514/564 |
| 5,605,929 | 2/1997 | Liao et al. | 514/456 |
| 5,670,154 | 9/1997 | Hara et al. | 424/195.1 |
| 5,674,907 | 10/1997 | Southan et al. | 514/634 |

OTHER PUBLICATIONS

Ahmad N, Srivastava RC, Agarwal R and Mukhtar H, Nitric oxide synthase and skin tumor promotion. *Biochem Biophys Res Commun* 232:328–331, 1997.

Baek KJ, Thiel BA, Lucas S and Stuehr DJ, Macrophage nitric oxide synthase subunits. *J Biol Chem* 268:21120–21129, 1993.

Chan MM, Ho CT and Huang HI, Effects of three dietary anti-inflammatory phytochemicals from tea, rosemary and turmeric on nitrite production through the nitric oxide pathway. *Cancer Lett* 96:23–29, 1995.

Chan MM, Fong D, Ho CT and Huang HI, Inhibition of inducible nitric oxide synthase gene expression and enzyme activity by epigallocatechin gallate, a natural product from green tea. *Biochem Pharmacol* 54:1281–1286, 1997.

Fiala ES, Sodum RS, Bhattacharya M and Li H, (–)-Epigallocatechin gallate, a polyphenolic tea antioxidant, inhibits peroxynitrite mediated formation of 8–oxodeoxyguanosine and 3–nitrotyrosine, *Experientia* 52:922–926, 1996.

Forstermann U, Pollack JS, Tracey WR and Nakane M, Isoforms of nitric oxide synthase: Purification and regulation. *Methods Enzymol* 233:258–264, 1994.

Ghosh DK and Stuehr DJ, Macrophage NO synthase: Characterization of isolated oxygenase and reductase domains reveals a head–to–head subunit interaction. *Biochemistry* 34:801–807, 1995.

Hevel JM and Marletta MA, Nitric oxide synthase assays. *Methods Enzymol* 233: 250–258, 1994.

Ho CT, Chen Q, Huang S, Zhang KQ and Rosen RT, Antioxidative effect of polyphenol extract prepared from various Chinese teas. *Prev Med* 21:520–525, 1992.

Klatt P, Schmidt M, Leopold E, Schmidt K, Werner ER and Mayer B, The pterine binding site of brain nitric oxide synthase. Tetrahydrobiopterin binding kinetics, specificity and allosteric interaction with the substrate domain. *J Biol Chem* 269:13861–13866, 1994.

Lin YL and Lin JK, (–)-Epigallocatechin–3–gallate blocks the induction of nitric oxide synthase by down–regulating lipopolysaccharide–induced activity of transcription factor nuclear factor–kB. *Mol Pharmacol* 52;465–472, 1997.

Mayer B, Klatt P, Werner ER and Schmidt K, Molecular mechanisms of inhibition of porcine brain nitric oxide synthase by the antinociceptive drug 7–nitro–indazole. *Neuropharmacology* 33: 1253–1259, 1994.

Nathan C, Inducible nitric oxide synthase: What difference does it make? *J Clin Invest* 100:2417–2423, 1997.

Pannala AS, Rice–Evans CA, Halliwell B and Singh S, Inhibition of peroxynitrite–mediated tyrosine nitration by catechin polyphenols. *Biochem Biophys Res Commun* 232: 164–168, 1997.

Siebert PD and Kellogg DE, PCR mimics: Competitive DNA fragments for use in quantitative PCR. In: *PCR2: A Practical Approach* (Eds. McPherson MJ, Hames BD and Taylor GR), pp. 135–148. IRL Press, Oxford, 1995.

Stuehr DJ, Structure–function aspects in the nitric oxide synthases. *Annu Rev Pharmacol Toxicol* 37;339–359, 1997.

Wang ZY, Das M, Bickers DR and Mukhtar H, Interaction of epicatechins derived from green tea with rat hepatic cytochrome P–450. *Drug Metab Dispos* 16: 98–103, 1988.

Wolff DJ and Gribin BJ, Interferon-g–inducible murine macrophage nitric oxide synthase: Studies on the mechanism of inhibition by imidazole agents. *Arch Biochem Biophys* 311:293–299, 1994.

Xie B, Shi H, Chen Q and Ho CT, Antioxidant properties of fractions and polyphenol constitutents from green, oolong and black teas. *Proc Natl Sci Counc Repub China B* 17:77–84, 1993.

*Primary Examiner*—Theodore J. Criares

[57] ABSTRACT

This invention is directed to a pharmacologically acceptable composition for inhibiting nitric oxide synthase in a mammal, which include catechin derivatives and a pharmaceutically acceptable carrier. The invention also concerns a method of inhibiting nitric oxide synthase, and treating various conditions where there is an advantage in inhibiting nitric oxide biosynthesis. The method includes the step of administering to a mammal a catechin derivative, such as epigallocatechin-3-gallate or a related polyphenol, in pure form or in a pharmaceutically acceptable carrier. The novel inhibitors inhibit nitric oxide synthase at the level of gene expression and enzyme activity.

10 Claims, 5 Drawing Sheets

(-) Epigallocatechin-3-gallate (-) Epicatechin-3-gallate (-) Epigallocatechin

METHOD OF INHIBITING NITRIC OXIDE SYNTHASE

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

1. Field of Invention

This invention relates to novel inhibitors of nitric oxide synthase (NOS) that act at the level of enzymatic activity inhibition. In particular, this invention relates to the treatment of acute and chronic inflammatory conditions by the administration of NOS inhibitors.

2. Background

Nitric oxide (NO) is a gas radical produced by the enzyme nitric oxide synthase (NOS). There are three NOS enzymes, or isoforms, in mammals. A low level of NO is continuously produced by isoforms I and III, the constitutive or cNOS that are activated by calcium and the calcium-binding protein calmodulin. The NO produced is functional in vascular and nervous systems, and is important in the regulation of blood pressure and in neurotransmission. A high level of NO is produced by isoform II, the inducible or iNOS that is regulated by gene expression. The high level of NO is functional in the immune system as a means of host defense.

In the immune system, NO produced by one particular type of leukocytes, namely the macrophages, contributes to leukocyte killing of bacteria, fungi and tumor cells. Although meant to be protective, excess NO and NO metabolites, or reactive nitrogen intermediates, may also contribute to the destructive aspects of an immune response, particularly in chronic inflammation, by non-specific destruction of cellular metabolic machinery within a circumscribed area of NO release. Such non-specific destruction, if excessive, can lead to any one of a number of inflammatory diseases or syndromes, inclusing autoimmune diseases, such is rheumatoid arthritis.

Interfering with the production of NO provides a means of modulating inflammatory reactions and of inhibiting destructive sequelae of a chronic inflammatory immune response. However, given that NO is highly reactive by nature, inhibitors which inhibit the NO radical directly would not be expected to be as effective as an inhibitor which blocks the synthesis of the NO radical.

A variety of inhibitors of the nitric oxide synthases has been reported, as seen from the following examples. U.S. Pat. No. 5,585,402 to Moncada and Palmer (1996) discloses N-monomethyl-L-arginine. U.S. Pat. No. 5,674,907 to Southan, Salzman and Szabo (1997) discloses mercapto derivatives as NOS inhibitors. U.S. Pat. No. 5,449,688 to Wahl, Allen and McCartney-Francis (1995) discloses a method of treating chronic inflammatory diseases using compounds including nitric oxide synthase inhibitors. However, these compounds are mostly generated by chemical synthesis, and may have additional adverse effects besides inhibiting the NOS enzymes. Hence, inhibitors from natural sources are being sought after. It is anticipated that additional compounds may prove to have fewer side effects and greater selectivity in inhibiting the inducible nitric oxide synthase enzyme.

Epigallocatechin-3-gallate (EGCG) is the major polyphenol from green tea. Since tea is one of the most widely consumed beverages, second only to water, tea-derived EGCG may be much safer. Several beneficial effects of EGCG are known, as seen from the following examples. U.S. Pat. Nos. 5,318,986 and 5,670,154 both granted to Hara and Honda (1994, 1997) disclose that tea polyphenols including EGCG inhibit the enzyme activity of alpha amylase and tyrosinase. U.S. Pat. No. 5,605,929 to Liao and Liang (1997) discloses catechins including EGCG inhibit the enzyme activity of 5 alpha reductase. U.S. Pat. No. 5,391,568 to Chung (1995) discloses that EGCG inhibits lung cancer in a mammal. However, the effect of EGCG on the level of enzyme activity of nitric oxide synthase is unknown.

It is the object of the present invention to provide a method for the treatment of chronic and acute inflammatory conditions. More specifically, it is an object of the present invention to provide a method for the treatment of conditions wherein an agent that inhibits nitric oxide synthase is administered.

These and other objects and advantages of the present invention, as well as additional inventive features, will be apparent from the description of the invention provided herein.

BRIEF SUMMARY OF THE INVENTION

This invention is directed to a pharmacologically acceptable composition for inhibiting nitric oxide synthase (NOS) in a mammal. The composition includes a catechin derivative and a pharmaceutically acceptable carrier, with the active agent present in the composition in an effective amount to inhibit NOS in the mammal.

The present invention provides a method for treating a mammal, preferably a human, having an inflammatory condition, especially chronic, wherein an effective amount of an agent, which is capable of decreasing the amount of nitric oxide present, is administered. Preferably, the agent is an inhibitor of NOS. More preferably, the NOS inhibitor is a catechin derivative, such as the green tea polyphenol epigallocatechin-3-gallate (EGCG).

The invention may be more specifically regarded as inhibiting NOS at the level of gene expression and enzyme activity. Catechin derivatives, such as EGCG from green tea, competitively inhibit binding of the substrate arginine and the cofactor tetrahydrobiopterin to the NOS enzyme; and they also decrease the messenger RNA level of NOS. The invention for the composition and the method includes the catechin EGCG, both in natural and synthetic forms, and its structural derivatives generated by chemical and molecular biological processes such as via combinatorial library.

DETAILED DESCRIPTION OF THE INVENTION

Figure 1:
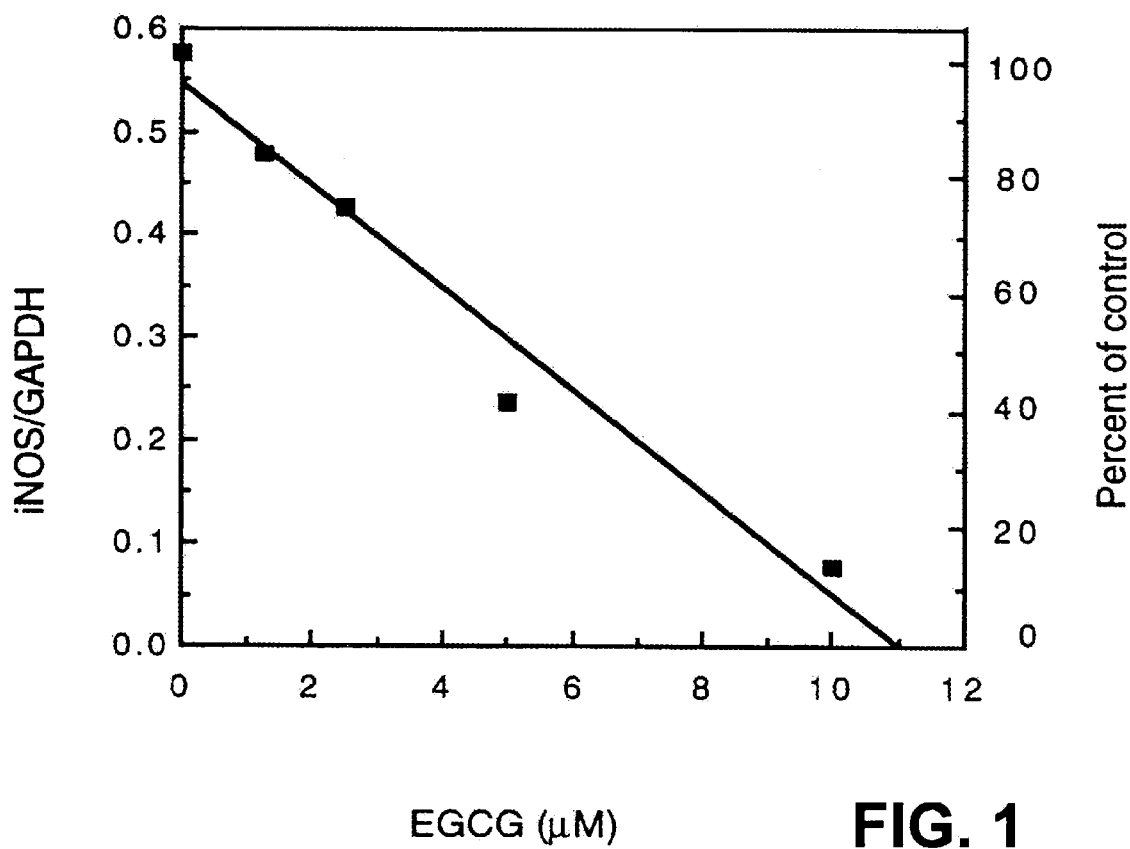
FIG. 1 is a graph of the effect of epigallocatechin gallate (EGCG) on the relative level of inducible nitric oxide synthase (iNOS) gene expression in murine peritoneal cells.

This invention is directed to a pharmacologically acceptable composition for inhibiting nitric oxide synthase (NOS) in a mammal. The composition includes a catechin derivative and a pharmaceutically acceptable carrier, with the catechin derivative present in the composition in an effective amount to inhibit NOS in the mammal. The invention is also directed to a method of inhibiting NOS in a mammal, which includes the step of administering to the mammal a catechin derivative in pure form or in a pharmaceutically acceptable carrier.

Suitable catechin derivatives for use in the composition or method can be isolated from natural sources such as green tea. This invention discloses that the green tea polyphenol epigallocatechin-3-gallate (EGCG) is an inhibitor of nitric oxide synthase (NOS). Additional NOS isoform-specific inhibitors can be generated from EGCG using chemical and molecular biological manipulations such as the combinatorial library approach.

The invention may be more specifically regarded as inhibiting NOS at the dual level of gene expression and enzyme activity. Catechin derivatives, such as EGCG from green tea, competitively inhibit binding of the substrate arginine and the cofactor teirahydrobiopterin to the NOS enzyme; and they also decrease the messenger RNA level of NOS.

Epigallocatechin-3-gallate (EGCG), or a structurally-related catechin derivative, in pure form or in a pharmacologically acceptable carrier, will find benefit in treating conditions and disorders where there is an advantage in inhibiting the nitric oxide synthase enzyme and selectively inhibiting the inducible form. Said catechin derivatives may be used in treat circulatory shock; they may also be beneficial for patients receiving therapy with cytokines such as TNF, IL-1 and IL-2 or therapy with cytokine-inducing agents, or as a short term immunosuppression in transplant therapy. In addition, the derivatives may be useful to inhibit NO synthesis in patients suffering from inflammatory conditions in which an excess of NO contributes to the pathophysiology of the condition, such as adult respiratory distress syndrome and myocarditis, for example.

There is also evidence that an NO synthase enzyme may be involved in the pathophysiology of autoimmune and/or inflammatory conditions such as arthritis, rheumatoid arthritis and systemic lupus erythematosus and in insulin-dependent diabetes mellitus, and therefore, catechin derivatives may prove helpful in treating these conditions.

Furthermore, it is now clear that there are a number of additional inflammatory and non-inflammatory diseases that are associated with NO over-production. Examples of such physiological disorders include: inflammatory bowel diseases such as ileitis, ulcerative colitis and Crohn's disease; inflammatory lung disorders such as asthma and chronic obstructive airway disease; inflammatory disorders of the eye including corneal dystrophy, trachoma and onchocerciasis; chronic inflammatory disorders of the gum including periodontitis; chronic inflammatory disorders of the joints including arthritis and osteoarthritis, tuberculosis, leprosy and nephrosis; disorders of the skin including sclerodermatitis, psoriasis and eczema; inflammatory diseases of the central nervous system, including chronic demyelinating diseases such as multiple sclerosis, dementia including AIDS-related neurodegeneration and Alzheimer's disease, encephalomyelitis and viral or autoimmune encephalitis; autoimmune diseases including immune-complex vasculitis, systemic lupus and erythematodes; and disease of the heart including ischemic heart disease and cardiomyopathy. Additional disease that may benefit from the use of EGCG derivatives include adrenal insufficiency; hypercholesterolemia; atherosclerosis; bone disease associated with increased bone resorption, e.g. osteoporosis, preeclampsia, eclampsia, uremic complications; chronic liver failure, non-inflammatory diseases of the central nervous system including stroke and cerebral ischemia; and various forms of cancer.

Pharmaceutical formulations of the catechin derivative may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All methods include the steps of bringing into association the active compound with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion; or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules, and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation the active ingredient is conveniently delivered from an insufflator, nebulizer pressurized packs or other convenient means of delivering an aerosol spray. Pressurized packs may comprise a suitable propellant such as dichlorodifluoromethane, carbon dioxide or other suitable gas. In the case of a pressurized aerosol, the dosage unit may be determined by providing a valve to deliver a metered amount.

Alternatively, for administration by inhalation or insufflation, the active ingredient may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

The active ingredient may also be used in combination with other therapeutic agents, for example, anti-inflammatory agents, particularly non-steroidal anti-inflammatory drugs (NSAIDs), and vasodilator prostaglandins.

It should be understood that in addition to the ingredients particularly mentioned above, the formulations of this invention may include other agents conventional in the art having regard to the type of formulation in question, for example those suitable for oral administration may include flavoring agents.

Preferred unit dosage formulations are those containing an effective dose, as recited below, or an appropriate fraction thereof, of the active ingredient.

For each of the aforementioned conditions, the NOS inhibitors of the invention may be administered orally or via injection at a dose of from 1 to 250 mg/kg per day. The dose range for adult humans is generally from 50 mg to 17.5 g/day and preferably 150 mg to 3 g/day. Tablets or other forms of presentation provided in discrete units may conveniently contain an amount which is effective at such dosage or as a multiple of the same, for instance, units containing 5 mg to 500 mg, usually around 100 mg to 500 mg.

The pharmaceutical composition preferably is administered orally or by injection (intravenous or subcutaneous), and the precise amount administered to a patient will be the responsibility of the attending physician. However, the dose employed will depend upon a number of factors, including the age and sex of the patient, the precise disorder being treated, and its severity. Also the route of administration may vary depending upon the condition and its severity.

The following examples are provided by way of illustration, and are not intended to limit the scope of the invention.

EXAMPLE 1

Effect of Epigallocatechin Gallate on Inducible Nitric Oxide Synthase Gene Expression The green tea polyphenol epigallocatechin-3-gallate (EGCG) can modulate the level of expression of the inducible nitric oxide synthase (iNOS) gene. Addition of 1–10 $\mu$M EGCG to lipopolysaccharide (LPS)- and interferon-$\gamma$(IFN$\gamma$)-activated mouse peritoreal cells reduced iNOS mRNA expression concentration dependently, to 82–14%, as measured by relative reverse transcription-polymerase chain reaction (RT-PCR).

A. MATERIALS AND METHODS

1. Materials

Purification of EGCG (over 95% pure) and other catechins was performed according to Xie et al. (1993). Recombinant murine IFN$\gamma$ was provided by Dr. Sidney Pestka of the University of Medicine and Dentistry of New Jersey-Robert Wood Johnson Medical School. (The item is also commercially available.)

2. Gene expression assay

Non-elicited peritoneal exudate cells were obtained from BALB/c mice (Jackson Laboratories) and were cultured at $10^6$/mL as described by Chan et al. (1995). They were stimulated by the addition of 0.01 $\mu$g/mL LPS from *Salmonella typhosa* (Difco Laboratories) and 10 units/mL of IFN$\gamma$. At 4 hr after stimulation, total RNA was isolated with a Purescript RNA isolation kit (Gentra). RT-PCR was performed to determine the level of iNOS gene expression. From each sample, 300 ng of RNA was reverse-transcribed using 100 units MMLV reverse transcriptase, 20 units RNase inhibitor, 0.6 mM dNTP, and 0.4 mM Oligo(dT$_{16}$) (Promega). Then PCR analyses were performed on the aliquots of the cDNA preparations for detecting iNOS and glyceraldehyse 3-phosphate dehydrogenase (GAPDH) gene expression. The reactions occurred in a 50 $\mu$L volume, for 23 cycles, with 10 mM Tris-HCl, pH 8.3, 50 mM KCl, 1.5 mM MgCl$_2$, 0.3 mM dNTP, 2.0 units of Taq DNA polymerase, and 50 pmol of 5' and 3' primers. Murine iNOS and GAPDH 5' and 3' primers were purchased from Clontech and used according to manufactures protocols. The products were then separated on 1.6% agarose gel, stained with ethidium bromide, and the intensity of the bands was determined by scanning (Siebert and Kellogg 1995).

B. RESULTS AND DISCUSSION

When activated murine peritoneal macrophages were incubated with EGCG, the gene expression of iNOS was inhibited. This effect was verified by the RT-PCR technique. Relative RT-PCR showed that at 1, 3, 5, and 10 $\mu$M, EGCG reduced iNOS mRNA expression in a concentration-dependent manner, to 82, 74, 41, and 14% (FIG. 1). This inhibition was specific because reduction in mRNA expression of GAPDH, a housekeeping gene, was not observed. Nonetheless, we have used the iNOS/GAPDH ratio to determine the degree of inhibition so as to adjust for minor differences in RT efficiency among the samples.

We have been interested in the effect of EGCG on NO production. Previously, we reported that EGCG reduces NO production by LPS- and IFN$\gamma$-induced mouse peritoneal cells, as measured by nitrite accumulation in the culture medium (Chan et al. 1995). The above finding shows that one of the mechanisms is via EGCG inhibition of iNOS gene expression. EGCG reduction of NO production has recently been confirmed by Lin and Lin (1997), who also reported inhibition of iNOS gene expression independently.

EXAMPLE 2

Effect of Epigallocatechin Gallate on Inducible Nitric Oxide Synthase Enzyme Activity Not only does EGCG inhihit iNOS gene expression, EGCG also inhibits iNOS enzyme activity. Addition of 50–750 $\mu$M EGCG, in a concentration-dependent manner, inhibited the enzyme activity of iNOS, to 85–14%, as measured by citrulline formation. EGCG competitively inhibits the binding of the substrate arginine and the co-factor tetrahydrobiopterin to the iNOS enzyme.

A. MATERIALS AND METHODS

1. Enzyme extraction

Murine iNOS was extracted from the RAW 264.7 murine macrophages (from the American Type Culture Collection). The cells were stimulated with 20 units/mL cf IFNγ and 0.5 μg/mL LPS, incubated for 4 hr, and then harvested. The washed cells were lysed in 50 mM MOPS buffer (pH 7.0) which contained 1 mM EGTA, 100 mM NaCl, 0.1% 3-[(3-cholamidopropl)dimethylammonio]-2-hydroxy-1-propanesulfonate (CHAPSO), 0.2 mM phenylmethylsulfonyl fluoride, 50 mM E-64, and 1 mM leupeptin. After passing through Sephadex G-100 (Pharmacia) to remove arginine, NADPH, and unbound tetrahydrobiopterin, the supernatant was concentrated by ultrafiltration using Centricon 30 microconcentrators (Amicon) (Forstermann et al. 1994; Wolff and Gribin 1994). Murine iNOS, 100,000 g fraction, was also purchased from Cayman.

2. Citrulline assay for nitric oxide synthase

Enzyme inhibition studies for iNOS were conducted in 50 mM HEPES buffer (pH 7.4) containing 1 mM calcium chloride, 1 mM magnesium acetate and 100 mM NADPH. [$^3$H]arginine (New England Nuclear), tetrahydrobiopterin (Biomol), and EGCG were added at the indicated concentrations. Reactions were terminated by the addition of AG 50WX8 resin (Bio-Rad) in HEPES-EDTA buffer (pH 5.5). Enzyme activity was measured by monitoring the conversion of [$^3$H]arginine to [$^3$H]citrulline (Hevel and Marletta 1994). Reactions were allowed to occur at 37° C. for 10–20 min since time-course analyses had shown that the reaction was linear under these conditions. Background was determined by the level of radioactivity in a reaction mixture from which iNOS was omitted. This amount was subtracted from the level detected in the experimental samples. Enzyme activity, i.e. the amount of citrulline formed, was deduced from the specific activity of the [$^3$H]arginine.

B. RESULTS AND DISCUSSION

Figure 2:
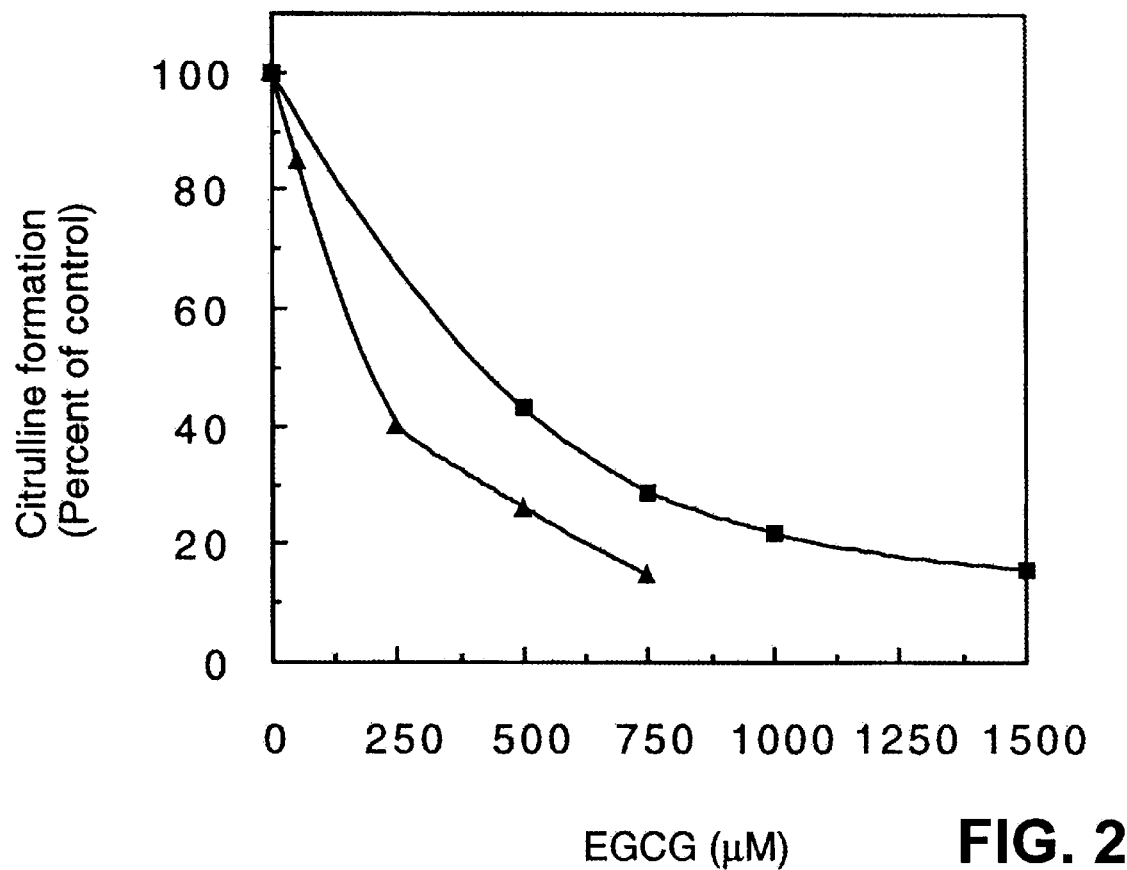
FIG. 2 is a graph of the effect of EGCG on the enzyme activity of iNOS in cell lysate and in a partially purified fraction.

The structure of NOS resembles a fusion of a cytochrome P450-like oxygenase at the amino terminal and cytochrome P450-like reductase at the carboxyl end (Gliosh et al. 1995). Since it has been shown that EGCG and other green tea catechins bind to various hepatic cytochrome P450s and inhibit P450-dependent functions, we investigated whether EGCG may inhibit NOS activity by inhibiting enzyme activity (Wang et al. 1988). In a concentration-dependent manner, EGCG inhibited the enzyme activity of iNOS, either in the form of crude extract from stimulated RAW 264.7 cells (FIG. 2, squares), or as 100,000 g fraction (FIG. 2, triangles) that was arginine- and NADPH-free. Addition of 50, 250, 500, and 750 μM EGCG inhibited citrulline formation to 85, 40, 27, and 14%, respectively, when the reaction occurred in 0.135 μM arginine and 60 μM tetrahydrobiopterin with 126 pmol/min of the 100,000 g iNOS preparation. The half-maximal effective concentration was 150 μM.

Figure 3:
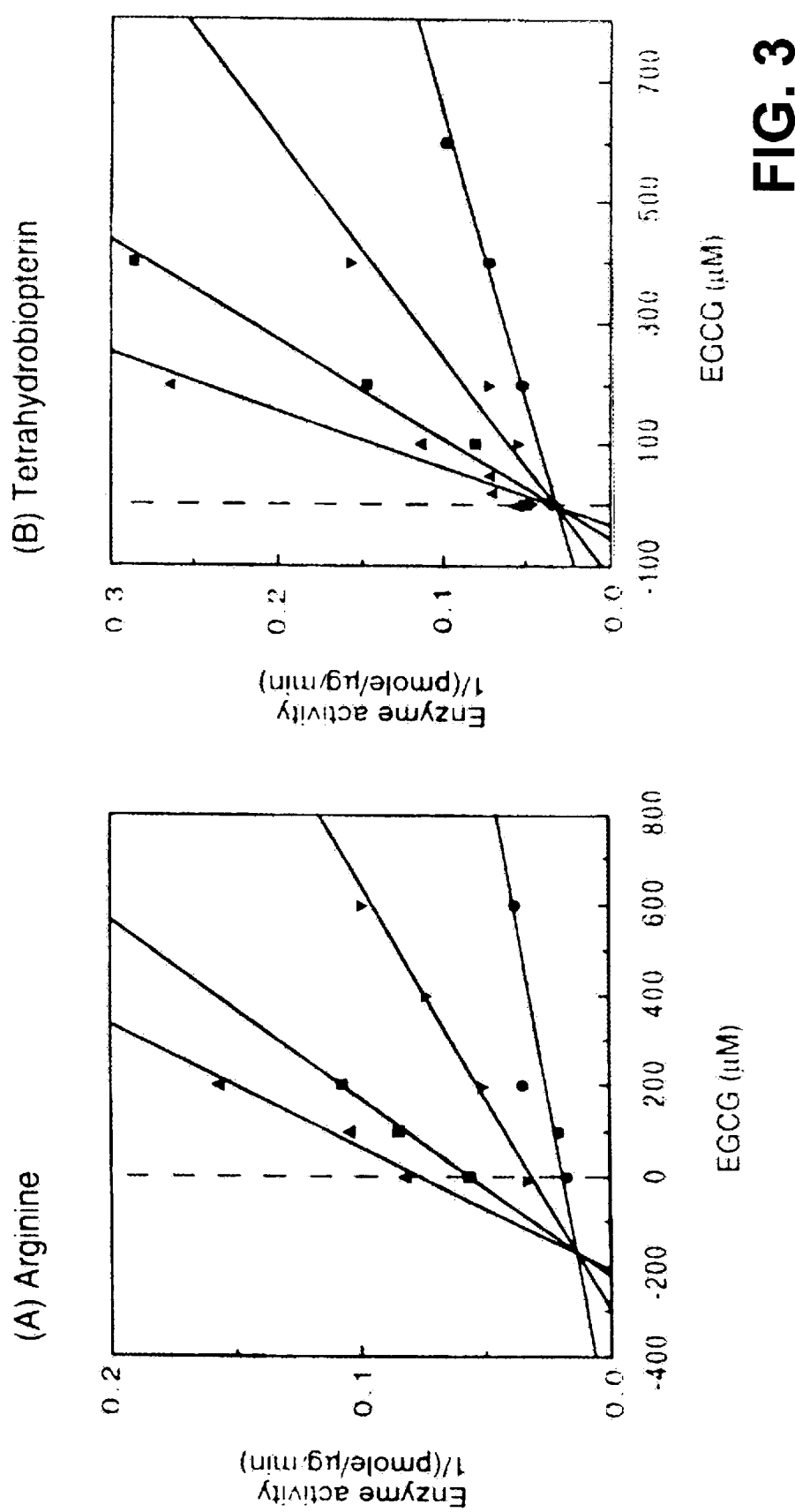
FIG. 3 is a graph on the kinetic analysis of the action of EGCG on iNOS activity with respect to arginine (substrate) and tetrahydrobiopterin (co-factor).

To elucidate the molecular mechanism of inhibition, the kinetic properties of the inhibition were explored. With respect to substrate, iNOS (100,000 g fraction) was incubated with 100, 200, 400, and 600 μM EGCG and 0.068 (FIG. 3A, triangles), 0.090 (squares), 0.135 (inverted triangles), and 0.270 μM (circles) arginine. The potency of the inhibition decreased with increasing concentrations of arginine (FIG. 3A). A Dixon plot of the rate of citrulline formation as a function of EGCG concentration revealed a competitive pattern of inhibition. A series of lines intersected at a common point above the abscissal axis, indicating an apparent $K_i$ of 130 pmol/min.

NOS molecules have to be associated into dimers in order to have enzymatic activity (Baek et al. 1993). After association, the oxygenase domains at the amino terminal form the catalytic center that binds arginine, tetrahydrobiopterin, and heme. Interdependently, arginine and tetrahydrobiopterin enhance each other's affinity for binding (Klatt et al. 1994). Therefore, we proceeded to examine whether EGCG interferes with tetrahydrobiopterin binding. Similarly, iNOS (100,000 g fraction) was incubated with 100, 200, 400, or 600 μM EGCG and 12 (FIG. 3B, triangles), 60 (squares), 90 (inverted triangles), or 125 μM (circles) tetrahydrobiopterin (FIG. 3B). Although 100,000 g fractions contained inherently bound tetrahydrobiopterin, a Dixon plot indicated that EGCG decreased the maximal velocity of iNOS in a competitive manner. It is likely that EGCG may inhibit by binding to the catalytic domain, and its action on iNOS resembles that of nitroindazole on nNOS. Nitroindazole is an arginine and tetrahydrobiopterin competitive inhibitor of nNOS enzyme activity that has been used in many studies to deduce the biochemical structure of the enzyme (Mayer et al. 1994).

As shown from the data above, EGCG competitively inhibits the binding of both the substrate arginine and the co-factor tetrahydrobiopterin to the iNOS enzyme. It can inhibit iNOS enzyme activity in a concentration-dependent manner. In addition, EGCG also inhibits iNOS gene expression (FIG. 1). To our knowledge, EGCG is the first compound reported to inhibit at both levels of gene expression and enzyme activity (Chan et al. 1997).

EXAMPLE 3

Effect of Related Tea Polyphenols on Inducible Nitric Oxide Synthase Enzyme Activity EGCG and related compounds were tested for inhibition of iNOS enzymatic activity. This structure-function analysis of inhibition has suggested that the gallate moiety is important for this inhibitory action.

A. MATERIALS AND METHODS

Purification of tea catechin polyphenols was performed according to Xie et al. (1993). Enzyme preparation and assay were followed as described in the Methods section of Example 2.

B. RESULTS AND DISCUSSION

Figure 4:
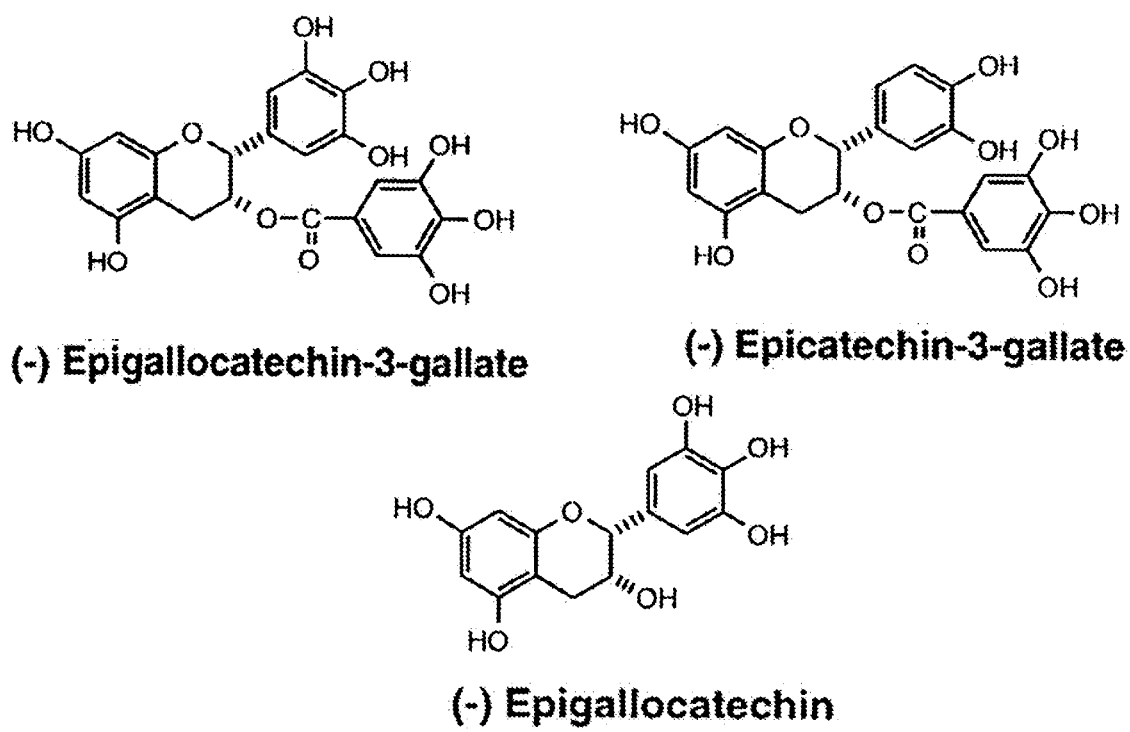
FIG. 4 is a graph on the effect of EGCG, epigallocatechin and epicatechin gallate on iNOS enzymatic activity, together with their chemical structures.
Figure 4:
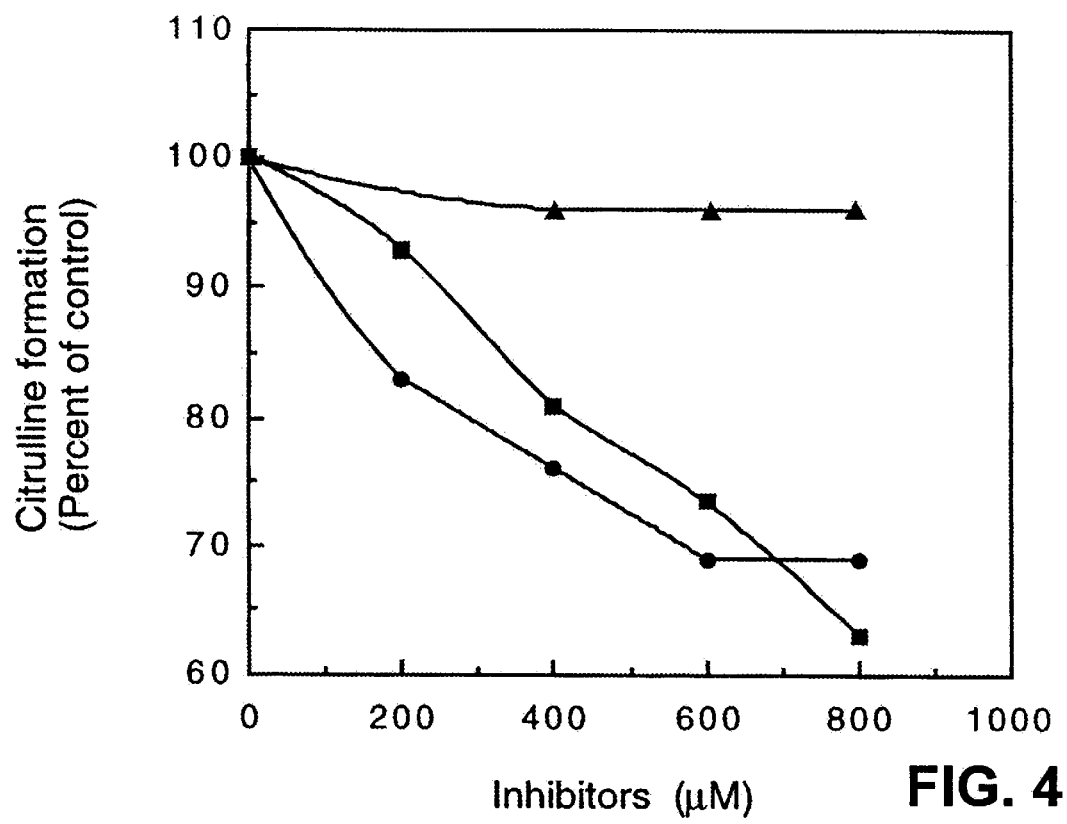

Green tea contains several epicatechins, EGCG, epicatechin-gallate (ECG), epigallocatechin (EGC) and epicatechin (EC), that are similar in chemical structure. Their relative efficacy for inhibiting iNOS activity was evaluated so as to determine the structure-function relationship. FIG. 4 is representative of three experiments that were performed with 0.270 μM arginine, 125 μM tetrahydrobiopterin, and 126 pmol/min of iNOS. EGCG (squares) and ECG (circles), at 800 μM, reduced citrulline formation to 62 and 68%, respectively, whereas EGC (triangles) was non-effective, with 96% citrulline formation. This suggests that the gallate structure may play a critical role in the inhibition. Moreover, since all three of the compounds have anti-oxidative capacity and their order of potency is EGCG>ECG>EGC, the fact that EGCG and ECG were equally potent suggested that it is unlikely for the anti-oxidative action to determine the efficacy of iNOS inhibition, although the possibility of it having a role is not ruled out (Ho et al., 1992).

EXAMPLE 4

Effect of Epigallocatechin Gallate on Constitutive Nitric Oxide Synthase Enzyme Activity The effect of EGCG on constitutive NOS has been studied. Addition of 50–750 μM EGCG, in a concentration-dependent manner, inhibited the enzyme activity of neuronal nitric oxide synthase (nNOS), to 93–56%, as measured by citrulline formation.

A. MATERIALS AND METHODS

Purification of EGCG was performed according to Xie et al. (1993). Neuronal NOS sample preparation and enzyme activity assay were described in the Methods section of Example 2, with the following modifications. For nNOS, fresh brains from BALB/c mice were homogenized in a 5-fold volume of 50 mM Tris-HCl (pH 7.5) that contained 1 mM EDTA, 5 mM 2-mercaptoethanol and then were centrifuged at 100,000 g for 1 hr, and then the sample was passed through the Sephadex G-100 column. For the nNOS enzyme assay, 5 $\mu$M flavin mononucleotide, 5 $\mu$M flavin adenine dinucleotide, 10 $\mu$g/mL calmodulin (Calbiochem) and 1.25 mM DTT were incorporated in the reaction mixture.

B. RESULTS AND DISCUSSION

Figure 5:
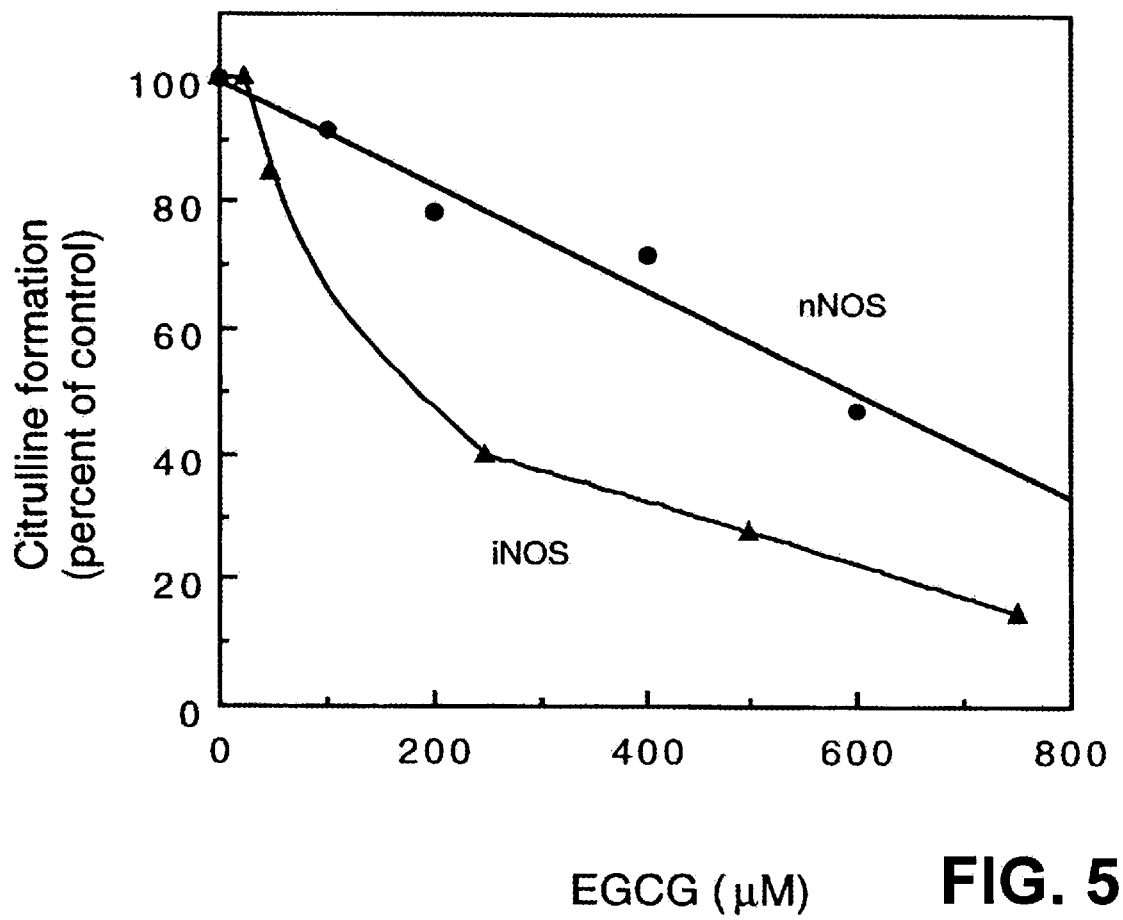
FIG. 5 is a graph on the effect of EGCG on the enzyme activity of iNOS and neuronal NOS activity (from murine brain lysate).

We explored the effect of EGCG on nNOS. Neuronal NOS was prepared as 100,000 g fraction from mouse brain extract. Addition of 100, 200, 400, and 600 $\mu$M EGCG to nNOS inhibited citrulline formation by 93, 79, 51, and 56%, respectively, when compared with the control in which EGCG was omitted (FIG. 5). Although the result seems to indicate that EGCG was more effective against iNOS than nNOS, its differential selectivity and $K_i$ for the two isoforms remain to be determined. This is because here the enzymes used were partially purified and the conditions that were required for the two isoforms were not equivalent. For measuring nNOS activity, 0.135 $\mu$M arginine and 125 $\mu$M tetrahydrobiopterin were used. It has been debated that the differenfial regulation of the action of NOS isoforms may be under indirect control, through the intracellular availability of arginine, tetrahydrobiopterin, and calcium, e.g. nNOS requires calcium/cadmodulin binding. In addition, in vivo, the difference in enzyme life-span, shorter for nNOS and longer for iNOS, may also be a contributing factor. Nonetheless, the present result suggests that EGCG is capable of inhibiting both nNOS and iNOS.

The principal novelty and significance of catechin derivatives is our discovery that it is possible to have a small molecule that inhibits the NOS enzyme at both the level of gene expression and enzyme activity. Presently, most investigators look for iNOS inhibitors that block at one of these two potential therapeutic targets. iNOS is mainly regulated by gene expression; however, once produced, iNOS remains chronically activaled and continually produces NO for the lifetime of the enzyme. Being able to reduce NO production at both iNOS mRNA accumulation and enzyme activity, EGCG will provide a distinctive advantage over inhibitors that may work at only one level, especially in conditions where immediate reduction of NO is necessary. The action of green tea polyphenols (including EGCG) in vivo has been reported by Ahmed et al. (1997) in their study of modulation of constitulive NOS activity in mouse skin during skin tumor promotion (at a topical dose of 3 mg per animal). Furthermore, the therapeutic potential of EGCG is even greater in light of the reports that it may possibly inhibit peroxynitrite, a product from reaction between NO and $O_2^-$ that mediates protein damage by the formation of nitrotyrosine and DNA damage by the formation of oxodeoxyguanosine (Fiala et al. 1997; Pannala et al. 1997).

In summary, from structure-function aspects of nitric oxide synthases, especially for the inducible isoform (Nathan, 1997; Stuehr 1997), epigallocatechin-3-gallate (EGCG) and related catechins are useful inhibitors, in the inhibition of gene expression and enzyme activity, and possibly even in peroxynitrite formation.

REFERENCES (The references listed below and all references cited herein are incorporated herein by references to the extent that they supplement, explain, provide a background for, or teach methodology, techniques, and/or compositions employed herein.)

Ahmad N, Srivastava R C, Agarwal R and Mukhtar H, Nitric oxide synthase and skin tumor promotion. *Biochem Biophys Res Commun* 232: 328–331, 1997.

Baek K J, Thiel B A, Lucas S and Stuehr D J, Macrophage nitric oxide synthase subunits. *J Biol Chem* 268: 21120–21129, 1993.

Chan M M, Ho C T and Huang H I, Effects of three dietary anti-inflammatory phytochemicals from tea, rosemary and turmeric on nitrite production through the nitric oxide pathway. *Cancer Lett* 96: 23–29, 1995.

Chan M M, Fong D, Ho C T and Huang H I, Inhibition of inducible nitric oxide synthase gene expression and enzyme activity by epigallocatechin gallate, a natural product from green tea. *Biochem Pharmacol* 54:1281–1286, 1997.

Fiala E S, Sodum R S, Bhattacharya M and Li H, (−)-Epigallocatechin gallate, a polyphenolic tea antioxidant, inhibits peroxynitrite mediated formation of 8-oxodeoxyguanosine and 3-nitrotyrosine. *Experientia* 52: 922–926, 1996.

Forstermann U, Pollack J S, Tracey W R and Nakane M, Isoforms of nitric oxide synthase: Purification and regulation. *Methods Enzymol* 233: 258–264, 1994.

Ghosh D K and Stuehr D J, Macrophage NO synthase: Characterization of isolated oxygenase and reductase domains reveals a head-to-head subunit interaction. *Biochemistry* 34: 801–807, 1995.

Hevel J M and Marletta M A, Nitric oxide synthase assays. *Methods Enzymcl* 233: 250–258, 1994.

Ho C T, Chen Q, Huang S, Zhang K Q and Rosen R T, Antioxidative effect of polyphenol extract prepared from various Chinese teas. *Prev Med* 21: 520–525, 1992.

Klatt P, Schmidt M, Leopold E, Schmidt K, Werner E R and Mayer B, The pterine binding site of brain nitric oxide synthase. Tetrahydrobiopterin binding kinetics, specificity and allosteric interaction with the substrate domain. *J Biol Chem* 269: 13861–13866, 1994.

Lin Y L and Lin J K, (−)-Epigallocatechin-3-gallate blocks the induction of nitric oxide synthase by down-regulating lipopolysaccharide-induced activity of transcription factor nuclear factor-κB. *Mol Pharmacol* 52;465–472, 1997.

Mayer B, Klatt P, Werner E R and Schmidt K, Molecular mechanisms of inhibition of porcine brain nitric oxide synthase by the antinociceptive drug 7-nitro-indazole. *Neuropharmacology* 33: 1253–1259, 1994.

Nathan C, Inducible nitric oxide synthase: What difference does it make? *J Clin Invest* 100: 2417–2423,1997.

Pannala A S, Rice-Evans C A, Halliwell B and Singh S, Inhibition of peroxynitrite-mediated tyrosine nitration by catechin polyphenols. *Biochem Biophys Res Commun* 232: 164–168,1997.

Siebert P D and Kellogg D E, PCR mimics: Competitive DNA fragments for use in quantitative PCR. In: *PCR2: A Practical Approach* (Eds. McPherson M J, Hames B D and Taylor G R), PP. 135–148. IRL Press, Oxford, 1995.

Stuehr D J, Structure-function aspects in the nitric oxide synthases. *Annu Rev Pharmacol Toxicol* 37; 339–359, 1997.

Wang Z Y, Das M, Bickers D R and Mukhtar H, Interaction of epicatechins derived from green tea with rat hepatic cytochrome P-450. *Drug Metab Dispos* 16: 98–103, 1988.

Wolff D J and Gribin B J, Interferon-γ-inducible murine macrophage nitric oxide synthase: Studies on the mechanism of inhibition by imidazole agents. *Arch Biochem Biophys* 311: 293–299, 1994.

Xie B, Shi H, Chen Q and Ho C T, Antioxidant properties of fractions and polyphenol constitutents from green, oolong and black teas. *Proc Natl Sci Counc Repub China B* 17: 77–84,1993.

What is claimed is:

1. A method of treating a nitric oxide-mediated inflammatory disorder comprising administering to a host in need thereof a therapeutically effective amount of a compound selected from the group consisting of epigallocatechin-3-gallate and epicatechin-3-gallate.

2. The method of claim 1 wherein the nitric oxide-mediated inflammatory disorder is diabetes.

3. The method of claim 1 wherein the nitric oxide-mediatd inflammatory disorder is periodontitis.

4. The method of claim 1 wherein the nitric oxide-mediated inflammatory disorder is vasculitis.

5. The method of claim 1 wherein the nitric oxide-mediated inflammatory disorder is inflammatory bowel disease.

6. The method of claim 1, wherein said compound is administered at 50 mg to 17.5 g/day.

7. A method of treating a disease selected from the group consisting of diabetes, periodontitis, vasculitis and inflammatory bowel disease in a mammal in need thereof which comprises administering to the mammal an effective amount to treat said disease, of a gallated catechin compound selected from the group consisting of epigallocatechin-3-gallate and epicatechin-3-gallate.

8. The method of claim 7, wherein said catechin compound is epigallocatechin-3-gallate.

9. The method of claim 7, wherein said catechin compound is epicatechin-3-gallate.

10. A method for the inhibition of nitric oxide synthase in a subject in need of such inhibition which comprises the administration of an effective amount of nitric oxide synthase inhibitor wherein the inhibitor is selected from the group consisting of epigallocatechin-3-gallate and epicatechin-3-gallate.

* * * * *